United States Patent
Walter et al.

(10) Patent No.: US 8,632,654 B2
(45) Date of Patent: Jan. 21, 2014

(54) HARDENER FOR EPOXY RESINS

(71) Applicants: Henkel AG & Co. KGaA, Duesseldorf (DE); Henkel Corporation, Rocky Hill, CT (US)

(72) Inventors: Pablo Walter, Duesseldorf (DE); Mustapha Benomar, Duisburg (DE); Stefan Keriling, Eppelheim (DE); Timothy Walsh, Weymouth, MA (US); Rainer Schoenfeld, Duesseldorf (DE)

(73) Assignees: Henkel AG & Co. KGAA, Duesseldorf (DE); Henkel US IP LLC, Rocky Hill, CT (US)

( * ) Notice: Subject to any disclaimer, the term of this patent is extended or adjusted under 35 U.S.C. 154(b) by 0 days.

(21) Appl. No.: 13/756,844

(22) Filed: Feb. 1, 2013

(65) Prior Publication Data

US 2013/0146223 A1   Jun. 13, 2013

Related U.S. Application Data

(63) Continuation of application No. PCT/EP2011/061217, filed on Jul. 4, 2011.

(60) Provisional application No. 61/369,943, filed on Aug. 2, 2010.

(51) Int. Cl.
*C07C 323/43* (2006.01)
*C09J 163/04* (2006.01)

(52) U.S. Cl.
USPC ........... 156/314; 564/500; 564/501; 524/217; 523/453; 525/438

(58) Field of Classification Search
USPC ................... 564/500, 501; 524/217; 523/453; 525/438; 156/314
See application file for complete search history.

(56) References Cited

U.S. PATENT DOCUMENTS 4,990,679 A    2/1991   Wolf et al.

FOREIGN PATENT DOCUMENTS

| | | |
|---|---|---|
| DE | 19729875 | 1/1998 |
| EP | 0370448 | 5/1990 |
| EP | 2006310 | 12/2008 |

OTHER PUBLICATIONS

International Search Report issued in connection with International Patent Application No. PCT/EP2011/061217 mailed on Dec. 27, 2011.

*Primary Examiner* — John Uselding
(74) *Attorney, Agent, or Firm* — Sun Hee Lehmann

(57) ABSTRACT

The present application is directed to use of a thioether compound, obtainable from a first educt that comprises at least two thiol groups and from a second educt that comprises at least one α,β-unsaturated amide group as well as at least one tertiary amine group, for the hardening of reactive resins.

11 Claims, No Drawings

HARDENER FOR EPOXY RESINS

The present invention relates to the use of specific thioether compounds as hardeners for reactive resins, to hardener compositions and two-component compositions that contain said compounds, and to a method for adhesively bonding materials in which said compounds are used.

Reactive resin systems have been successfully used for a long time as adhesives or repair compounds for consumers, do-it-yourselfers, and craftspeople, and in the aviation, automotive, or electrical industry as adhesives, sealants, or for the coating of surfaces, or have been utilized as resin systems with a number of different substances for the manufacture of composite materials. Hardenable formulations that contain mixtures of reactive resin and hardener are particularly suitable as structural adhesives.

The reactive resin systems known in the existing art are subdivided in principle into two classes. On the one hand, one-component systems are known; these contain a latent hardener that reacts only after suitable activation, for example by UV radiation or heat input, with the resins that are present. Also known are two-component systems in which the hardener is present packaged separately from the reactive resins until shortly before actual utilization.

One known group of hardeners that are usually used in two-component systems are the so-called mercaptan hardeners. These are usually polysulfides and polymercaptans having terminal thiol groups. Because these hardeners, considered of themselves, react only very slowly with the reactive resins, in particular the epoxy resins, catalysts are often also added to the hardener preparations. Amines or urea derivatives are often used as such catalysts. Such systems are often referred to colloquially as "five-minute" epoxy adhesives.

The object of the present invention was accordingly to develop a mercaptan-based hardener for reactive resins that exhibits satisfactory curing behavior even without the addition of catalysts, and additionally results in products that are also not inferior to the known mercaptan/catalyst-based curing products in terms of their mechanical properties, for example tensile shear strength.

It has now been found, surprisingly, that specific thioether group-containing compounds result in the desired combination of properties, namely sufficient self-catalyzed hardening speed and adhesive properties.

A first subject of the present invention is therefore the use of a thioether compound, obtainable from a first educt that comprises at least two thiol groups and from a second educt that comprises at least one $\alpha,\beta$-unsaturated amide group as well as at least one tertiary amine group, for the hardening of reactive resins.

A "hardener" is understood according to the present invention as a compound that produces crosslinking of the reactive resins. "Hardening" is accordingly understood as the process that brings about crosslinking of the reactive resins. A "hardener preparation" is understood according to the present invention as the agent prepared in ready-to-use fashion. Because the thioether compounds used according to the present invention are themselves capable of catalyzing the hardening reaction, it may be preferred according to the present invention if the hardener preparation contains the thioether compound according to the present invention as the only reactive substance.

For the instance in which the thioether compound used according to the present invention comprises free thiol groups, the entirely or partly deprotonated derivatives of these compounds are, according to the present invention, also encompassed within the scope of the present invention.

An essential property of the adhesive bonds that result from use according to the present invention of the specific thioether compound is the so-called tensile shear strength. This is determined by means of the following experimental setup: Two sandblasted, cold-rolled steel specimens are wetted with the adhesive being tested, with an overlap area of 2.5 cm$^2$ at a layer thickness of 0.2 mm, and bonded. After corresponding curing, the tensile shear strength of the adhesive is tested in accordance with DIN EN 1465 at a rate of 15 mm/min. It has proven to be advantageous according to the present invention if the adhesives exhibit, after they are cured, a tensile shear strength above 8 MPa, in particular above 10 MPa, at room temperature.

A further essential parameter of the use according to the present invention is the resulting processing time. The "processing time" is understood according to the present invention as the time span after initial mixing during which the adhesive composition can easily be processed, i.e. the mixture can still build up adhesion with the surfaces to be adhesively bonded. The processing time is determined, according to the present invention, as follows: At 25° C., 10 g of the application mixture to be tested is produced from the two individual components and thoroughly mixed for 2 minutes. The condition of the surface of the application mixture is then tested with the aid of a wooden spatula that is brought vertically onto the surface. The processing time has elapsed when the application mixture no longer adheres to the wooden spatula, i.e. when adhesive threads with a length of at least 1 cm no longer form on the spatula. It has proven to be particularly advantageous according to the present invention if the processing time is less than 30 minutes, preferably less than 10 minutes.

A specific thioether compound that can be obtained from a first educt that comprises at least two thiol groups, and from a second educt that comprises at least one $\alpha,\beta$-unsaturated amide group as well as at least one tertiary amine group, is used as a component essential to the invention.

The thioether compound according to the present invention is preferably formed without the addition of further compounds, for example catalysts, at room temperature or slightly elevated temperature (approx. 20° C. to approx. 90° C.). This reaction is preferably carried out at approx. 70° C. and with a reaction time from 2 to 4 hours. With regard to a concrete embodiment of a reaction of this kind, reference may be made at this juncture to the statements made in the context of the Examples section.

It is immaterial with regard to the reactivity of the compounds used according to the present invention whether only some of the thiol groups of the first educt are reacted or whether in fact all the thiol groups of the first educt are converted into thioether groups. On the contrary, both products whose thiol groups have been only partly reacted and products whose thiol groups have been completely reacted are suitable according to the present invention. The product mixtures that usually result in the context of such conversions are of course also suitable for carrying out the present invention, and are accordingly also encompassed.

It is possible according to the present invention that only one specific second educt which reacts with the thiol groups is present, i.e. that all the thiol groups encounter the same reaction partner during the reaction. It is, however, also possible according to the present invention for multiple second educts, which differ from one another, to be offered, and thus for inhomogeneously substituted thioether compounds to be formed.

Without intending to limit the invention to one specific reaction mechanism, it will be assumed that in the aforesaid reaction, a thioether group forms from at least one of the thiol groups of the first educt. Thioether compounds that comprise in the molecule
  a. at least one thioether group,
  b. if applicable, one or more thiol groups,
  c. at least one amide group, and
  d. at least one tertiary amine group
are accordingly preferred according to the present invention, provided that the thioether compound comprises at least two sulfur-containing functional groups selected from thioether groups and/or thiol groups.

It has proven particularly advantageous according to the present invention if the thioether compound carries at least one group of formula (I)

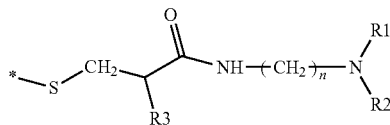

where
  R1 and R2, mutually independently, denote a $C_1$ to $C_{20}$ alkyl group,
  R3 denotes a hydrogen atom or a $C_1$ to $C_4$ alkyl group,
  n denotes a whole number from 1 to 20,
  providing that the group of formula (I) is bound via a carbon atom to the remainder of the molecule.

Examples of a branched or unbranched $C_1$ to $C_{20}$ alkyl group are the methyl, ethyl, propyl, isopropyl, n-butyl, sec-butyl, tert-butyl, pentyl, hexyl, octyl, 2-ethylhexyl, and lauryl groups. It is very particularly preferred according to the present invention if the residues R1 and R2 denote, mutually independently, a branched or unbranched $C_1$ to $C_4$ alkyl group. Propyl, ethyl, and methyl are particularly preferred $C_1$ to $C_4$ alkyl groups. A methyl group is a very particularly preferred alkyl group.

Thioether compounds having a group (I) in which R1 and/or R2 denotes a methyl group are particularly preferred.

It has proven advantageous according to the present invention if the residues R1 and R2 have identical meanings, in particular if both residues R1 and R2 denote a methyl group.

It is further preferred according to the present invention if the residue R3 denotes a hydrogen atom or a methyl group. Residues of formula (I) in which R3 denotes a methyl group are very particularly preferred.

It has further proven advantageous according to the present invention if n denotes a whole number from 1 to 5, in particular one of the numbers 1, 2, or 3, Residues of formula (I) in which n denotes the number 3 are very particularly preferred.

Very particularly preferred thioether compounds are obtained when compounds that comprise two or more thiol groups are reacted with dimethylaminopropyl methacrylamide (DMAPMA; CAS: 5205-93-6). This compound is notable for improved compatibility with the thiol compound, lower toxicity, its high boiling point, and its commercial availability.

An educt ratio in which 0.1 to 1 mol of reaction partner per mol of thiol groups is offered for the formation of thioether groups has proven particularly advantageous in this context. A ratio of 1 mol thiol groups to 0.2 to 1 mol reaction partner is particularly preferred.

The thiol group-containing educt can be, according to the present invention, both a monomeric compound, an oligomeric compound, or even a polymeric compound.

An "oligomer" is understood according to the present invention as a compound having fewer than 4 repeating units. A "polymer" is accordingly understood as a compound having 4 or more repeating units.

It is accordingly preferred according to the present invention if the thioether compound is a compound of formula (II)

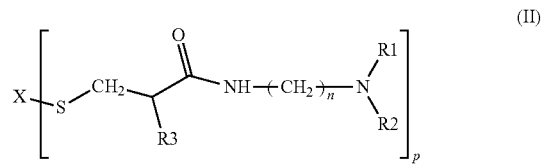

where
  R1 and R2, mutually independently, denote a $C_1$ to $C_{20}$ alkyl group,
  R3 denotes a hydrogen atom or a $C_1$ to $C_4$ alkyl group,
  n denotes a whole number from 1 to 20,
  p denotes a rational number from 1.0 to 5.0, and
  X denotes a p-valent residue that is respectively bound via a carbon atom to the functional group of formula (I), and if applicable comprises at least one thiol group and/or at least one thioether group,
  providing that X obligatorily comprises at least one thiol group and/or at least one thioether group when p=1.

With regard to the particularly preferred embodiments of the residues R1, R2, and R3 and of the number n, reference is explicitly made at this juncture to the statements above.

The residue X denotes, in a manner preferred according to the present invention, an oligomeric or polymeric residue.

It is further preferred if the residue X comprises alkylene diol units, in particular ethylene glycol units and/or propylene glycol units and/or butane diol units.

Residues X that comprise two or more alkylene diol units are very particularly preferred according to the present invention. In particular, residues X that contain two or more ethylene glycol units and/or two or more, in particular three, propylene glycol units are particularly preferred.

Because the thioether compounds preferred according to the present invention exhibit good effectiveness as a hardener for reactive resins regardless of the synthesis path selected, compounds of formula (II) that can be obtained from educts other than those described above are also encompassed according to the present invention.

A first group of first educts according to the present invention that comprise two or more thiol groups and, after reaction, yield the compounds according to the present invention of formula (II), is based on alkoxylated derivatives of glycerol. Glycerol derivatives having a degree of alkoxylation from 2 to 9 are particularly preferred according to the present invention. A degree of alkoxylation from 2 to 5 is very particularly preferred. In this group as well, propylene glycol and ethylene glycol are preferred alkylene diols. Propylene glycol is very particularly preferred in this embodiment.

A particularly preferred educt of this group is

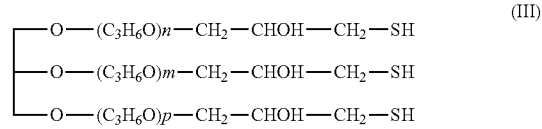

in which n, m, and p, mutually independently, each denote a whole number from 0 to 3, provided that the sum n+m+p denotes a whole number from 2 to 9, in particular a whole number from 2 to 5.

Thioether compounds that are obtained as a reaction product of a reaction of a compound of formula (III) with dimethylaminopropyl methacrylamide (DMAPMA) are particularly preferred according to the present invention. An educt ratio in which 0.1 to 1 mol DMAPMA per mol of thiol groups is offered for the formation of thioether groups has proven particularly advantageous in this context. A ratio of 1 mol thiol groups to 0.2 to 1 mol DMAPMA is particularly preferred.

A second group of such educts is derived from the polyalkylene diols. In the context of this group, polyalkylene diols having 2 to 5 alkylene diol units are particularly preferred. In this group as well, propylene glycol and ethylene glycol are preferred alkylene glycols. Ethylene glycol is particularly preferred in this embodiment.

A particularly preferred educt of this group is

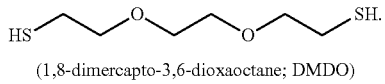

(1,8-dimercapto-3,6-dioxaoctane; DMDO)

Prepolymers that can be obtained from DMDO are likewise suitable educts according to the present invention.

Thioether compounds that are obtained as a reaction product of a reaction of 1,8-dimercapto-3,6-dioxaoctane, and/or a prepolymer thereof, with dimethylaminopropyl methacrylamide (DMAPMA) are particularly preferred according to the present invention. An educt ratio in which 0.1 to 1 mol DMAPMA per mol of thiol groups is offered for the formation of thioether groups has proven particularly advantageous in this context. A ratio of 1 mol thiol groups to 0.2 to 1 mol DMAPMA is particularly preferred.

The thioether compounds described here are used according to the present invention to harden reactive resins.

A "reactive resin" is understood according to the present invention as a compound that has an average functionality greater than 1. As a result of the reactive groups, the compound can be reacted with suitable hardeners and thereby hardened.

In principle, the thioether compound according to the present invention can be used to harden the reactive resins known in the existing art, as long as suitable reactivity exists. This is the case in particular for the isocyanate-based resins, acrylate- and methacrylate-based resins, anhydrides, and the epoxy-based systems. It has proven particularly advantageous according to the present invention if the thioether compounds are used to harden epoxy resins.

Epoxy resins hardenable according to the present invention in the context of the present invention are selected from epoxy resins of the bisphenol A type, epoxy resins of the bisphenol S type, epoxy resins of the bisphenol F type, epoxy resins of the phenol novolac type, epoxy resins of the cresol novolac type, epoxidized products of numerous dicyclopentadiene-modified phenol resins obtainable by the reaction of dicyclopentadiene with numerous phenols, epoxidized products of 2,2',6,6'-tetramethylbiphenol, aromatic epoxy resins such as epoxy resins having a naphthalene basic framework and epoxy resins having a fluorene basic framework, aliphatic epoxy resins such as neopentyl glycol diglycidyl ethers and 1,6-hexanediol diglycidyl ethers, alicyclic epoxy resins such as 3,4-epoxycyclohexylmethyl-3,4-epoxycyclohexane carboxylate and bis(3,4-epoxycyclohexyl)adipate, and epoxy resins having a hetero ring, such as triglycidyl isocyanurate.

Particularly preferred epoxy resins are the reaction products of bisphenol A and epichlorohydrin, the reaction products of phenol and formaldehyde (novolac resins) and epichlorohydrin, glycidyl esters, and the reaction product of epichlorohydrin and p-aminophenol.

Further preferred epoxy resins that are commercially obtainable are, in particular, octadecylene oxide, epichlorohydrin, styrene oxide, vinylcyclohexene oxide, glycidol, glycidyl methacrylate, diglycidyl ethers of bisphenol A (e.g. those obtainable under the commercial designations "Epon 828", "Epon 825", "Epon 1004", "Epon 1007", "Epon 1002", "Epon 1001", and "Epon 1010" of Hexion Specialty Chemicals Inc., "DER-331", "DER-332", "DER-334", "DER-354", "DER-732" and "DER-736" of Dow Chemical Co.), vinylcyclohexene dioxide, 3,4-epoxycyclohexylmethyl-3,4-epoxycyclohexene carboxylate, 3,4-epoxy-6-methylcyclohexylmethyl-3,4-epoxy-6-methylcyclohexene carboxylate, bis(3,4-epoxy-6-methylcyclohexylmethyl)adipate, bis(2,3-epoxycyclopentyl)ether, aliphatic epoxide modified with polypropylene glycol, dipentene dioxide, epoxidized polybutadiene (e.g. Krasol products of Sartomer), silicone resins containing epoxide functionality, flame-retardant epoxy resins (e.g. "DER-580", a brominated epoxy resin of the bisphenol type obtainable from Dow Chemical Co.), 1,4-butanediol diglycidyl ethers of a phenol/formaldehyde novolac (e.g. "DEN-431" and "DEN-438" of the Dow Chemical Co.), as well as resorcinol diglycidyl ethers (e.g. "Kopoxite" of the Koppers Company Inc.), bis(3,4-epoxycyclohexyl)adipate, 2-(3,4-epoxycyclohexyl-5,5-spiro-3,4-epoxy)cyclohexanemetadioxane, vinylcyclohexene monoxide, 1,2-epoxyhexadecane, alkyl glycidyl ethers such as, for example, $C_8$ to $C_{10}$ alkyl glycidyl ethers (e.g. "HELOXY Modifier 7" of Hexion Specialty Chemicals Inc.), $C_{12}$ to $C_{14}$ alkyl glycidyl ethers (e.g. "HELOXY Modifier 8" of Hexion Specialty Chemicals Inc.), butyl glycidyl ethers (e.g. "HELOXY Modifier 61" of Hexion Specialty Chemicals Inc.), cresyl glycidyl ethers (e.g. "HELOXY Modifier 62" of Hexion Specialty Chemicals Inc.), p-tert-butylphenyl glycidyl ethers (e.g. "HELOXY Modifier 65" of Hexion Specialty Chemicals Inc.), polyfunctional glycidyl ethers such as, for example, diglycidyl ethers of 1,4-butanediol (e.g. "HELOXY Modifier 67" of Hexion Specialty Chemicals Inc.), diglycidyl ethers of neopentyl glycol (e.g. "HELOXY Modifier 68" of Hexion Specialty Chemicals Inc.), diglycidyl ethers of cyclohexanedimethanol (e.g. "HELOXY Modifier 107" of Hexion Specialty Chemicals Inc.), trimethylolethane triglycidyl ethers (e.g. "HELOXY Modifier 44" of Hexion Specialty Chemicals Inc.), trimethylolpropane triglycidyl ethers (e.g. "HELOXY Modifier 48" of Hexion Specialty Chemicals Inc.), polyglycidyl ethers of an aliphatic polyol (e.g. "HELOXY Modifier 84" of Hexion Specialty Chemicals Inc.), polyglycol diepoxide (e.g. "HELOXY Modifier 32" of Hexion Specialty Chemicals Inc.), bisphenol F epoxies (e.g. "EPN-1138" or "GY-281" of Huntsman Int. LLC), 9,9-bis-4-(2,3-epoxypropoxy)phenylfluorenone (e.g. "Epon 1079" of Hexion Specialty Chemicals Inc.).

Further preferred commercially obtainable compounds are selected, for example, from Araldite™ 6010, Araldite™ GY-281™, Araldite™ ECN-1273, Araldite™ ECN-1280, Araldite™ MY-720, RD-2 of Huntsman Int. LLC; DENT™ 432, DEN™ 438, DEN™ 485 of Dow Chemical Co., Epon™ 812, 826, 830, 834, 836, 871, 872, 1001, 1031 etc. of Hexion Specialty Chemicals Inc. and HPT™ 1071, HPT™ 1079 likewise of Hexion Specialty Chemicals Inc., as novolac resins furthermore, for example, Epi-Rez™ 5132 of Hexion Specialty Chemicals Inc., ESCN-001 of Sumitomo Chemical, Quatrex 5010 of Dow Chemical Co., RE 305S of Nippon Kayaku, Epiclon™ N673 of DaiNipon Ink Chemistry, or Epicote™ 152 of Hexion Specialty Chemicals Inc.

Further epoxy resins can be, by preference, copolymers of acrylic acid esters with glycidol, for example glycidyl acrylate and glycidyl methacrylate with one or more copolymerizable vinyl compounds. Examples of such copolymers are 1:1 styrene/glycidyl methacrylate, 1:1 methyl methacrylate/glycidyl acrylate, and 62.5:24:13.5 methyl methacrylate/ethyl acrylate/glycidyl methacrylate.

Further usable epoxy resins are silicones having epoxide functionality, in particular cyclohexylepoxide groups, in particular those having a silicone basic framework. Examples are UV 9300, UV 9315, UV 9400, and UV 9425, all of which are supplied by GE Bayer Silicones.

In a preferred embodiment, the preparations according to the present invention encompass a mixture of several of the aforesaid epoxy resins.

Examples of such mixtures can encompass two or more molecular-weight distributions of epoxy-containing compounds, for example a low molecular weight (below 200), a moderate molecular weight (approx. 200 to 10,000), and a higher molecular weight (above approx. 10,000). Alternatively or additionally, the epoxy resin can contain a mixture of epoxy-containing materials of differing chemical nature (e.g. aliphatic or aromatic) or functionality (e.g. polar or nonpolar).

A second subject of the present invention is a hardener composition for reactive resins that contains at least one thioether compound according to the present invention as well as an accelerator that comprises at least one nitrogen atom.

Although the thioether compounds according to the present invention are notable for the fact that they exhibit an acceptable reaction time even without the addition of an accelerator component (autocatalysis), it can be preferred according to the present invention if an accelerator is present in the context of the reaction.

Preferred examples of such accelerators are catalytically active substituted ureas. These are, in particular, N,N'-(di-(3-dimethylaminopropyl)) urea. In principle, catalytically active tertiary acrylamines or alkylamines such as, for example, benzyldimethylamine, tris(dimethylamino)phenol, piperidine, or piperidine derivatives can also be used. In addition, a variety of (by preference, solid) imidazole derivatives can be used as catalytically active accelerators. Representatives that may be named are 2-ethyl-2-methylimidazole, N-butylimidazole, benzimidazole, and N—$C_1$ to —$C_{12}$ alkylimidazoles or N-arylimidazoles. Adducts of amino compounds with epoxy resins are also suitable as accelerating additives to the aforesaid hardeners. Suitable amino compounds are tertiary aliphatic, aromatic, or cyclic amines. Suitable epoxy compounds are, for example, polyepoxides based on glycidyl ethers of bisphenol A or F, or of resorcinol. Concrete examples of such adducts are adducts of tertiary amines such as 2-dimethylaminoethanol, N-substituted piperazines, N-substituted homopiperazines, N-substituted aminophenols with di- or polyglycidyl ethers of bisphenol A or F or of resorcinol.

Accelerators that are very particularly preferred according to the present invention are 2-dimethylaminoethanol, tris (dimethylaminomethyl)phenol, and N,N'-(di-(3-dimethylaminopropyl)) urea. The last-named accelerator is commercially obtainable, for example, under the trade names Capcure® EH 50 and Versamine® EH 50.

A third subject of the present invention is two-component compositions whose first preparation contains at least one reactive resin and whose second preparation contains at least one thioether compound according to the present invention.

With regard to the resins and thioether compounds particularly suitable in the context of this subject of the present invention, reference may be made explicitly at this juncture to the statements above.

In a preferred embodiment of this subject of the present invention, the first preparation of the two-component composition contains as a reactive resin a mixture of
 a) at least one epoxy group-containing reaction product of epichlorohydrin with polypropylene glycol which has an epoxy equivalent weight of at least 250 g/eq, and
 b) at least one epoxy group-containing reaction product of epichlorohydrin with a novolac resin which has an epoxy equivalent weight of at least 175 g/eq.

In a preferred embodiment, the first preparation contains 10 to 60 wt % of component a). A quantitative range from 25 to 45 wt % is very preferred. The quantitative indications refer in each case to the mixture of all reactive epoxy resins without the further formulation constituents.

In the context of the work on which this invention is based, it was possible to show that epoxy group-containing reaction products of epichlorohydrin with polypropylene glycol having an epoxy equivalent weight of at least 300 g/eq exhibit particularly advantageous properties.

Particularly preferred components a) are, according to the present invention, the reactive epoxy resins marketed under the commercial designations DER 372 (EEW 310-330 g/eq), DER 732P (EEW 310-330 g/eq) by the Dow company.

It is particularly advantageous according to the present invention if corresponding epoxy group-containing reaction products of epichlorohydrin with polypropylene glycol having an epoxy equivalent weight of less than 300 g/eq are contained at a proportion of at most 3 wt %, in particular at most 1 wt %, based in each case on the entire composition.

In a preferred embodiment, the first preparation of the two-component composition according to the present invention contains 10 to 85 wt % of component b). A quantitative range from 30 to 75 wt % is very preferred. The quantitative indications refer in each case to the mixture of all reactive epoxy resins without the further formulation constituents.

In the context of the work on which this invention is based, it was possible to show that epoxy group-containing reaction products of epichlorohydrin with a novolac having an epoxy equivalent weight of at least 180 g/eq, and in particular at least 190 g/eq, exhibit particularly advantageous properties.

Novolacs preferred according to the present invention are the polycondensation products of formaldehyde with phenol and/or cresol.

It has furthermore proven advantageous if the reaction products of epichlorohydrin with novolac have an epoxy functionality of at least 3, in particular of at least 3.5.

Reaction products of epichlorohydrin with novolac that have an epoxy equivalent weight of at least 175 g/eq and at the same time an epoxy functionality of at least 3 can be particularly convincing in terms of the objects of the present invention. Reaction products of epichlorohydrin and novolac having an epoxy equivalent weight of at least 180 g/eq and an epoxy functionality of at least 3, in particular reaction products of epichlorohydrin and novolac having an epoxy equivalent weight of at least 190 g/eq and an epoxy functionality of at least 3.5, are particularly preferred.

With these, the desired combination of properties—processability prior to curing, and adhesive strength after curing—is best achieved.

Particularly preferred components b) are, according to the present invention, the reactive epoxy resins marketed under the commercial designations DEN 439 (EEW 191-210 g/eq; functionality 3.8; Dow), Araldite ECN 1299 (cresol-formaldehyde-novolac; EEW 235 g/eq; functionality 2.5-5.5; Huntsman), Epikote 154 (EEW 176-181 g/eq; Hexion). DEN 439 is very particularly preferred according to the present invention.

It is particularly advantageous according to the present invention if corresponding reaction products of epichlorohydrin and novolac having an epoxy equivalent weight of less than 175 g/eq are contained at a proportion of at most 3 wt %, in particular a proportion of at most 1 wt %, based in each case on the entire composition.

In a preferred embodiment of the present invention, the epoxy resin mixture furthermore contains at least one epoxy group-containing reaction product of epichlorohydrin with bisphenol A which has an epoxy equivalent weight of at least 500 g/eq.

In this embodiment, first preparations that contain, based on the mass of all epoxy resins, the following components:
  a) 10 to 60 wt % of an epoxy group-containing reaction product of epichlorohydrin with polypropylene glycol which has an epoxy equivalent weight of at least 250 g/eq,
  b) 15 to 85 wt % of an epoxy group-containing reaction product of epichlorohydrin with a novolac resin which has an epoxy equivalent weight of at least 175 g/eq, and
  c) 0 to 70 wt % of an epoxy group-containing reaction product of epichlorohydrin with at least one bisphenol which has an epoxy equivalent weight of at least 500 g/eq,
are accordingly particularly preferred.

Compositions that contain, based on the mass of all epoxy resins, the following components:
  30 to 45 wt % of an epoxy group-containing reaction product of epichlorohydrin with polypropylene glycol which has an epoxy equivalent weight of at least 250 g/eq,
  30 to 45 wt % of an epoxy group-containing reaction product of epichlorohydrin with a novolac resin which has an epoxy equivalent weight of at least 175 g/eq, and
  10 to 40 wt % of an epoxy group-containing reaction product of epichlorohydrin with at least one bisphenol which has an epoxy equivalent weight of at least 500 g/eq,
are particularly preferred according to the present invention.

In the context of the work on which this invention is based, it was possible to show that epoxy group-containing reaction products of epichlorohydrin with bisphenol A having an epoxy equivalent weight of at least 560 g/eq exhibit particularly advantageous properties.

Epoxy group-containing reaction products of epichlorohydrin with bisphenol A which have an epoxy equivalent weight of at least 500 g/eq that are particularly preferred according to the present invention are epoxy resins marketed under the commercial designations:
  Epikote® 1002 (EEW 575 to 700 g/eq; epoxy functionality 2; Hexion),
  DER® 662E (EEW 590 to 630 g/eq; epoxy functionality 2),
  Epon® 1002F (EEW 600 to 700 g/eq; epoxy functionality 2),
  DER® 662UH (EEW 675 to 750 g/eq; epoxy functionality 2),
  DER® 663U (EEW 730 to 820 g/eq; epoxy functionality 2),
  DER® 664U (EEW 875 to 955 g/eq; epoxy functionality 2),
  Epon® 1009F (EEW 2300 to 3800 g/eq; epoxy functionality 2; Hexion),
  Epon® 1007F (EEW 1700 to 2300 g/eq; epoxy functionality 2; Hexion),
  Epon® 1004F (EEW 800 to 950 g/eq; epoxy functionality 2; Hexion),
  DER® 692H (EEW 660 to 720 g/eq; epoxy functionality 2; Dow),
  DER® 692 (EEW 660 to 720 g/eq; epoxy functionality 2; Dow).

The products marketed under the commercial designations Epikote® 1002, DER® 662E, and Epon® 1002F are very particularly preferred according to the present invention. Epon® 1002F is very particularly preferred according to the present invention.

It is particularly advantageous according to the present invention if corresponding epoxy group-containing reaction products of epichlorohydrin with bisphenol A which have an epoxy equivalent weight below 500 g/eq are contained in the compositions at a proportion of at most 3 wt %, in particular at a proportion of at most 1 wt %, based in each case on the entire composition.

In toxicological terms in particular, it has proven to be advantageous if the compositions according to the present invention contain, in addition to the aforesaid epoxy group-containing reaction products a), b), and c) that are essential to the invention, less than 3 wt %, in particular less than 1 wt %, of further epoxy group-containing reaction products, based in each case on the entire preparation.

In a particularly preferred embodiment of this subject, the mixture of the epoxy resins is made up of
  a) 10 to 60 wt % of an epoxy group-containing reaction product of epichlorohydrin with polypropylene glycol which has an epoxy equivalent weight of at least 250 g/eq,
  b) 15 to 85 wt % of an epoxy group-containing reaction product of epichlorohydrin with a novolac resin which has an epoxy equivalent weight of at least 175 g/eq, and
  c) 0 to 70 wt % of an epoxy group-containing reaction product of epichlorohydrin with at least one bisphenol which has an epoxy equivalent weight of at least 500 g/eq,
the quantities of constituents a), b), and c) adding up to 100 wt %.

In a very particularly preferred embodiment of this subject, the mixture of the epoxy resins is made up of
  a) 30 to 45 wt % of an epoxy group-containing reaction product of epichlorohydrin with polypropylene glycol which has an epoxy equivalent weight of at least 250 g/eq,
  b) 30 to 45 wt % of an epoxy group-containing reaction product of epichlorohydrin with a novolac resin which has an epoxy equivalent weight of at least 175 g/eq, and
  c) 10 to 40 wt % of an epoxy group-containing reaction product of epichlorohydrin with at least one bisphenol which has an epoxy equivalent weight of at least 500 g/eq,
the quantities of constituents a), b), and c) adding up to 100 wt %.

The thioether compounds are used as hardeners preferably at a ratio of 1 thiol/thioether equivalent hardener per 1 to 3 epoxy equivalent. This means that the application mixture by preference exhibits an excess of reactive epoxy groups with respect to the reactive thiol groups and thioether groups.

In order to improve fracture behavior, in particular at temperatures below 0° C., the two-component preparations according to the present invention can contain one or more different so-called toughness improvers or "tougheners."

Such tougheners are known to those skilled in the art of epoxy adhesives. They can be selected, for example, from: thermoplastic isocyanates or polyurethanes, rubber particles, in particular those having a core-shell structure, and block copolymers, in particular those that contain a first polymer block having a glass transition temperature below 15° C. and a second polymer block having a glass transition temperature above 25° C. Such block copolymers are by preference selected from those in which a first polymer block is selected from a polybutadiene or polyisoprene block, and a second polymer block is selected from a polystyrene or polymethyl methacrylate block. Specific examples thereof are block copolymers having the following block structure: styrene-butadiene-(meth)acrylate, styrene-butadiene-(meth)acrylic acid esters, ethylene-(meth)acrylic acid ester-glycidyl (meth) acrylic acid ester, ethylene-(meth)acrylic acid ester-maleic acid anhydride, methyl methacrylate-butyl acrylate-methyl methacrylate.

It has furthermore proven advantageous according to the present invention if the two-component compositions according to the present invention contain, in addition to the mixture of epoxy resins and the hardener according to the present invention, at least one inorganic and/or organic filler.

Fillers preferred according to the present invention are, for example, the various ground or precipitated chalks, carbon black, calcium-magnesium carbonates, talc, barite, and in particular silicate fillers of the aluminum-magnesium-calcium silicate type, for example wollastonite, chlorite.

For weight reduction, the preparation can also contain, in addition to the aforesaid "normal" fillers, so-called lightweight fillers. These can be selected from the group of the hollow metal spheres such as, for example, hollow steel spheres, hollow glass spheres, fly ash (fillite), hollow plastic spheres based on phenol resins, epoxy resins, or polyesters, expanded hollow microspheres having a wall material made of (meth)acrylic acid ester copolymers, polystyrene, styrene/(meth)acrylate copolymers, and in particular of polyvinylidene chloride as well as copolymers of vinylidene chloride with acrylonitrile and/or (meth)acrylic acid esters, ceramic hollow spheres, or organic lightweight fillers of natural origin such as ground nut shells, for example the shells of cashew nuts, coconuts, or peanuts, as well as cork flour or coke powder. Particularly preferred in this context are those lightweight fillers, based on hollow microspheres, that ensure high compressive strength in the cured preparation.

In addition, the curable preparations according to the present invention can contain further usual adjuvants and additives such as, for example, plasticizers, rheology adjuvants, wetting agents, adhesion promoters, aging protection agents, stabilizers, and/or color pigments.

The two preparations of the two-component composition according to the present invention must be stored separately from one another until immediately before utilization.

This can preferably be done by packaging in separate containers. Removal of the preparation can then be accomplished immediately before utilization. This can be accomplished by manually measuring out the requisite quantities from storage vessels, for example drums.

In addition to purely manual measuring, dispensing can also be accomplished using simple manual dispensing units or even fully automated systems. Such systems are marketed, for example, by the Loctite® company. Examples of such automated systems are volumetric double gear pumps, double precision piston dispensers, double screw pump dispensers, or drum pump systems.

In a particularly preferred embodiment of the present invention, the preparations according to the present invention are offered in corresponding cartridges having a volume ratio of 1:1, 1:2, or 1:10 (component having epoxy resin mixture: component having a thioether compound). The selection of such double cartridges is intended, according to the present invention, to ensure consistent dispensing and thus a constant mixing ratio between the two components. The cartridges according to the present invention can be emptied, upon utilization, with the aid of simple manual dispensing units, but also using pneumatic and/or completely automated systems.

A fourth subject of the present invention is therefore a dispensing system that comprises two separate containers which, separately from one another, contain the first and the second component of the compositions according to the present invention, as well as a dispensing apparatus.

In another packaging form, the two components of the composition according to the present invention can be coextruded and accordingly packaged so as to be present directly next to one another until utilization. The two components must then be thoroughly mixed with one another at the time of utilization. This can be accomplished, for example, by kneading the coextrudates.

A fifth subject of the present invention therefore relates to the two-component compositions according to the present invention that are packaged as a coextrudate.

A sixth subject is furthermore the cured product of the two-component composition according to the present invention.

A seventh subject of the present invention is a method for adhesively bonding materials, in which
a) if applicable, the surfaces of the materials to be adhesively bonded are cleaned and/or pretreated,
b) a hardener composition containing at least one thioether compound according to the present invention is mixed with a second preparation that contains at least one reactive resin,
c) the resulting usable preparation is applied onto at least one of the material surfaces to be adhesively bonded,
d) the material surfaces to be adhesively bonded are then joined together, and
e) lastly, the applied usable preparation is cured at ambient temperatures between −10° C. and 80° C., by preference between 15° C. and 30° C.

At this juncture as well, reference is explicitly made with regard to preferred embodiments to the statements in the context of the other subjects of the present invention.

EXEMPLIFYING EMBODIMENTS

1 Manufacturing the Thio Compounds According to the Present Invention

Capcure® 3-800 (278 g/eq thiol EW) was made ready under a nitrogen atmosphere in a 250 ml three-neck flask and heated to 70° C., and 16.51 g DMAPMA (dimethylaminopropyl methacrylamide; M=170 g/mol) was slowly dripped in. Stirring was then performed for at least 2 hours at 70° C.

| Sample | Capcure® 3-800 (g) | DMAPMA (g) | Thiol EW:M(DMAPMA) |
|---|---|---|---|
| A-1 | 90 | 16.51 | 1:0.3 |
| A-2 | 90 | 55.04 | 1:1 |
| A-3 | 90 | 27.52 | 1:0.5 |
| A-4 | 90 | 11.01 | 1:0.2 |

In all the samples, the DMAPMA content after 2 hours of reaction time was <1.5 wt % (determined by HPLC analysis); after 4 hours of reaction time the DMAPMA content was only <0.4 wt %.

The thiol EW is indicated using the [eq/g] unit, and is defined as:

thiol EW [eq/g]=1/mercaptan number [meq/g]/1000).

The mercaptan number is determined by the manufacturer.

Manufacturing the Adhesives

The following two-component adhesives were manufactured and cured, and their tensile shear strengths determined:

| Sample | Resin mixture | Hardener | Additive | TSS (N/mm$^2$) | Processing time (min) |
|---|---|---|---|---|---|
| K-1 | 2.38 g DEN ®439<br>2.38 g DER ®732<br>1.19 g Epikote ® 1002 | 4.23 g A-3 | — | 13.53 | 4 |
| K-2 | 2.21 g DEN ®439<br>2.44 g DER ®732<br>1.16 g Epikote ® 1002 | 4.23 g A-1 | — | 10.39 | 5 |
| K-3 | 2.14 g DEN ®439<br>2.14 g DER ®732<br>0.58 g Epikote ® 1002 | 5.13 g A-2 | — | 12.29 | 3.5 |
| K-4 | 2.35 g DEN ®439<br>2.35 g DER ®732<br>1.18 g Epikote ® 1002 | 4.12 g A-2 | — | 9.38 | 5 |
| K-5 | 2.30 g DEN ®439<br>2.30 g DER ®732<br>1.15 g Epikote ® 1002 | 4.21 g A-1 | 0.04 g TETA (triethylenetetramine) | 15.42 | 4.5 |
| K-5 | 1.76 g DEN ®439<br>1.76 g DER ®732<br>0.88 g Epikote ® 1002 | 3.24 g A-1 | 2.06 g Luzenac ® 2<br>0.29 g Cabosil ® TS-720 | 20.00 | 4.5 |
| K-6 | 4.76 g DER ® 331 | 5.24 g A-1 | — | 11.19 | 2 |

1.1 List of Raw Materials Used

Cabosil® TS-720 Silicon dioxide, pyrogenic amorphous silicic acid; manufacturer: Cabot Capcure® 3-800 Mercaptan-terminated liquid polymer; mercaptan number at least 3.0 meq/g; mercaptans equivalent weight 278 g/eq.; manufacturer: Cognis DEN® 439 Reaction product of epichlorohydrin with a phenol/formaldehyde novolac; EEW 200 g/eq; epoxy functionality ±3.8; manufacturer: Dow DER® 331 Reaction product of bisphenol A with epichlorohydrin; EEW 187 g/eq; manufacturer: Dow DER® 732 Reaction product of epichlorohydrin with polypropylene glycol; EEW 320 g/eq; manufacturer: Dow Epikote® 1002 Reaction product of epichlorohydrin with bisphenol A; EEW 638 g/eq; manufacturer: Hexion;

Luzenac® 2 Natural association of talc, chlorite, and dolomite; manufacturer: Luzenac Group Versamine® EH-30 2,4,6-tris(dimethylaminomethyl)phenol; 100% active substance content; manufacturer: Cognis.

1.2 Determination of Tensile Shear Strengths

To determine the tensile shear strengths, the adhesives were applied onto two sandblasted, cold-rolled steel specimens with an overlap area of 2.5 cm$^2$ and a layer thickness of 0.2 mm, and the two specimens were bonded to one another. The specimens were then cured for 7 days at room temperature. After that period the tensile shear strength of the adhesive was tested in accordance with DIN EN 1465 at a rate of 15 mm/min. The values obtained are noted in the table above.

With all the resins (or resin mixtures), the thio compounds according to the present invention yielded adhesive bonds having a satisfactory tensile shear strength.

1.3 Determination of Processing Time

For the determination of processing time, 10 g of each adhesive mixture was placed in a dish. At frequent intervals, a wooden spatula was dipped into the adhesive mixture (perpendicularly to the surface of the adhesive mixture) and pulled out again. The processing time is the time period between mixing and that withdrawal of the spatula at which no further adhesive threads occur upon withdrawal.

The invention claimed is:

1. A hardener composition for hardening a reactive resin of a two component curable composition, comprising a thioether compound, wherein the thioether compound is a first educt comprising at least two thiol groups; a second educt comprising at least one α,β-unsaturated amide group as well as at least one tertiary amine group; or a mixture of the first educt and the second educt.

2. The hardener composition according to claim 1, wherein the thioether compound is a molecule comprising:
   a. at least one thioether group,
   b. optionally, one or more thiol groups,
   c. at least one amide group, and
   d. at least one tertiary amine group,
   providing that the thioether compound comprises at least two sulfur-containing functional groups selected from thioether groups and/or thiol groups.

3. The hardener composition according to claim 1, wherein the thioether compound carries at least one group of formula (I)

$$*-S-CH_2-\underset{R3}{\underset{|}{C}}-\overset{O}{\overset{\|}{C}}-NH-(CH_2)_n-N\begin{smallmatrix}R1\\R2\end{smallmatrix} \quad (I)$$

where

R1 and R2, mutually independently, are a $C_1$ to $C_{20}$ alkyl group,

R3 is a hydrogen atom or a $C_1$ to $C_4$ alkyl group, n is a whole number from 1 to 20, providing that the group of formula (I) is bound via a carbon atom to the remainder of the molecule.

4. The hardener composition according to claim 1, wherein the thioether compound is a compound of formula (II)

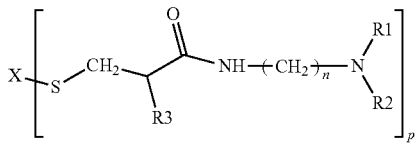
(II)

where
R1 and R2, mutually independently, are a $C_1$ to $C_{20}$ alkyl group,
R3 is a hydrogen atom or a $C_1$ to $C_4$ alkyl group,
n is a whole number from 1 to 20,
p is a rational number from 1.0 to 5.0, and
X is a p-valent residue that is respectively bound via a carbon atom to the functional group of formula (I), and optionally comprises at least one thiol group and/or at least one thioether group,
providing that X obligatorily comprises at least one thiol group and/or at least one thioether group when p=1.

5. The hardener composition according to claim 4, wherein R1 and R2 denote a methyl group, and/or
R3 denotes a methyl group, and/or
n denotes the whole number 3, and/or
X denotes an oligomeric or polymeric residue.

6. The hardener composition according to claim 4, wherein the residue X comprises alkylene diol units.

7. The hardener composition according to claim 1 further including an accelerator that comprises at least one nitrogen atom.

8. A two-component curable composition comprising a reactive resin composition and separately the thioether compound according to claim 1.

9. The two-component curable composition of claim 8, wherein the reactive resin is an epoxy resin.

10. A cured reaction product of the two-component composition according to claim 8.

11. A method for adhesively bonding materials, comprising:
providing a reactive resin composition;
providing the thioether compound of claim 1;
mixing the reactive resin composition and the thioether compound to form a curable composition;
applying the curable composition onto a first material surface to be adhesively bonded;
disposing a second material surface to be adhesively bonded onto the applied adhesive; and
curing the applied curable composition at temperatures between −10° C. and 80° C.

* * * * *